United States Patent [19]

Smith et al.

[11] Patent Number: 4,994,144

[45] Date of Patent: Feb. 19, 1991

[54] METHOD FOR INCREASING THE BULK OF CREPED TISSUE

[75] Inventors: Michael J. Smith, Neenah; Fung-Jou Chen, Appleton, both of Wis.

[73] Assignee: Kimberly-Clark Corporation, Neenah, Wis.

[21] Appl. No.: 435,646

[22] Filed: Nov. 13, 1989

[51] Int. Cl.$^5$ ............................................. D21H 25/00
[52] U.S. Cl. .................................... 162/111; 162/197; 162/207
[58] Field of Search ....................... 162/111, 207, 197; 156/183

[56] References Cited

U.S. PATENT DOCUMENTS

| Re. 28,459 | 7/1975 | Cole et al. | 162/115 X |
|---|---|---|---|
| 3,097,994 | 7/1963 | Dickens et al. | 162/297 |
| 3,291,678 | 12/1966 | Enloe et al. | 162/113 |
| 3,615,976 | 10/1971 | Endres et al. | 156/83 |
| 3,925,127 | 12/1975 | Yoshioka | 156/183 X |

FOREIGN PATENT DOCUMENTS 775300 5/1957 United Kingdom .

OTHER PUBLICATIONS

"The Calendering of Paper Containing Synthetic Pulp-Wood Blends", *Paper Technology and Industry*, Oct. 1975.

*Primary Examiner*—David A. Simmons
*Assistant Examiner*—Thi Dang
*Attorney, Agent, or Firm*—G. E. Croft

[57] ABSTRACT

The bulk of creped tissue products, such as facial and bath tissue, can be increased by steaming the tissue while stressed in the machine direction of the tissue.

16 Claims, No Drawings

METHOD FOR INCREASING THE BULK OF CREPED TISSUE

BACKGROUND OF THE INVENTION

In the manufacture of tissue products, such as facial tissue, bath tissue, and paper toweling, it is generally desireable to impart as much bulk as possible to the final product. Most typically, bulk is increased by embossing the tissue web after the web has been creped. However, embossing has its drawbacks in that it increases manufacturing costs and can substantially degrade the strength of the web.

SUMMARY OF THE INVENTION

It has now been discovered that the bulk of creped tissue webs can be increased simply by steaming the creped web while under tension. Steaming can be utilized to increase bulk with or without embossing. Besides its inherent simplicity, the method of this invention does not significantly degrade the strength of the web and, in some cases, may actually increase the strength of the web. In a continuous tissuemaking process in which the creped tissue web is wound onto one or more rolls prior to converting, care must be taken not to compress the web too soon after the steam treatment so that the web can be sufficiently dried. Otherwise the web may lose its bulk gains and become stiff due to additional bond formation.

For purposes herein, a creped tissue web is a creped web having a finished basis weight of from about 5 to about 40 pounds per 2880 square feet and comprising one or more plies, each of which can have one or more layers. Preferably the web consists primarily of cellulosic papermaking fibers. Typical creped tissue webs are, without limitation, wet pressed or through dried webs suitable for use as facial tissue, bath tissue, or household paper towels.

Steam suitable for use in the method of this invention can be subcooled, saturated or superheated. The temperature and moisture content of the steam must be such to elongate the creped web when the creped web is under 1 gram per inch of applied tension in the machine direction.

The amount of tension applied to the web during the steam treatment can be about 1 gram per lineal inch of width or greater, depending upon the nature of the steam and provided the web does not break. Naturally the upper limit of the amount of tension will depend largely upon the strength of the particular web. For facial and bath tissue, the amount of tension is preferably from about 1 gram per inch of width to about 15 grams per inch of width. For paper toweling, the amount of tension is preferably from about 1 gram per inch of width to about 100 grams per inch of width.

The length of time the creped web is exposed to the steam treatment can be almost instantaneous in a fast moving continuous process and would preferably be about 1 second or less, although treatment times can be longer, such as from about 1 to about 5 seconds. Treatment times will depend upon the nature of the steam, the amount of tension and the strength of the tissue web.

EXAMPLE

Air dry creped tissues having a blended furnish composition of 40% northern softwood bleached kraft fibers and 60% hardwood bleached kraft fibers were taped to a crossbar and suspended under tension in the machine direction of the tissue using glass rods light enough to prevent elongation before steaming but heavy enough to prevent buckling of the sample during or after steaming. Glass rod weights in the range of from about 2.4 to about 6.8 grams per inch have been used satisfactorily, the specific glass rod weight depending upon the particular tissue web being tested. While suspended, each tissue was humidified with saturated steam using a hand held steamer which was employed with a slow sweeping motion across and down the tissue to relax the crepe. Both sides of the tissue were humidified, regardless of the number of plies. The steaming process took about 30 seconds to treat the entire sample due to the relatively narrow coverage provided by the steamer. The resulting tissue was slightly wet to the touch after the steam treatment. After steaming, the tissue sample was allowed to air dry for about 5 minutes to come to equilibrium. Thereafter the properties of the tissue sample were measured. The results are set forth in the Table below. The control sample was not treated with steam, whereas test samples No. 1 and 2 were steam treated as described above. Web thickness is expressed in inches and bulk is expressed in cubic feet per 100 pounds. Both were measured in accordance with a standard test procedure (TAPPI Standard T411Os-68) using a TMI Model 549 thickness tester manufactured by Testing Machines Incorporated, Amityville, N.Y., except that the thickness tester utilized an anvil diameter of 2 inches and a load of 80 grams per square inch.

TABLE

| | (2-Ply Wet Pressed Facial Tissue) | | | | |
|---|---|---|---|---|---|
| Sample | Applied Tension (grams/inch) | TMI Thickness (2-Plies) | TMI Thickness (Each Ply) | TMI Bulk (2-Plies) | TMI Bulk (Per Ply) |
| Control | — | 0.0065 | 0.0046 | 8.4 | 11.9 |
| 1 | 2.4 | 0.0095 | 0.0055 | 12.4 | 14.3 |
| 2 | 4.1 | 0.0090 | 0.0054 | 12.0 | 14.4 |

The results clearly show a substantial increase in thickness and bulk for the steamed tissues over the Control. In addition, the steam-treated tissues appeared to exhibit an increase in perceived softness while slightly increasing in strength. The geometric mean tensile strength of the Control sample was about 570 grams per 3 inches of width, whereas the geometric mean tensile for both test samples was about 600 grams per 3 inches of width. Because the test samples were elongated during the steam treatment (2.7% for Sample No.1 and 6.8% for Sample No. 2), their finished basis weight decreased from 18.6 pounds per 2880 square feet to 18.4 and 18.0 pounds per 2880 square feet, respectively.

While this invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations which fall within the spirit and broad scope of the appended claims.

We claim:

1. A method of making a tissue product comprising contacting a dried creped tissue web with steam while the web is under tension in the machine direction, wherein the bulk of the web is increased.

2. The method of claim 1 wherein the amount of tension is from about 1 to about 100 grams per inch of width.

3. The method of claim 1 wherein the amount of tension is from about 1 to about 15 grams per inch of width.

4. The method of claim 1 wherein the steam is sub-cooled steam.

5. The method of claim 1 wherein the steam is saturated steam.

6. The method of claim 1 wherein the steam is superheated steam.

7. The method of claim 1 wherein the tissue product is a two-ply tissue.

8. The method of claim 1 wherein the tissue product is a single-ply tissue.

9. A continuous method for making a tissue product in which a tissue web is formed from an aqueous slurry of paper making fibers, dried, creped, and wound onto a roll, said method further comprising contacting the creped tissue web with steam while the creped web is under tension in the machine direction and allowing the steamed web to dry prior to being wound onto said roll, wherein the bulk of the creped web is increased relative to the same web prior to steaming.

10. The method of claim 9 wherein the amount of tension is from about 1 to about 100 grams per inch of width.

11. The method of claim 9 wherein the amount of tension is from about 1 to about 15 grams per inch of width.

12. The method of claim 9 wherein the steam is sub-cooled steam.

13. The method of claim 9 wherein the steam is saturated steam.

14. The method of claim 9 wherein the steam is superheated steam.

15. The method of claim 9 wherein the tissue product is a two-ply tissue.

16. The method of claim 9 wherein the tissue product is a single-ply tissue.

* * * * *